United States Patent [19]

Roman

[11] 4,230,863

[45] Oct. 28, 1980

[54] INSECTICIDAL SULFONIUM SALTS

[75] Inventor: Steven A. Roman, Oakdale, Calif.

[73] Assignee: Shell Oil Company, Houston, Tex.

[21] Appl. No.: 582,575

[22] Filed: Jun. 2, 1975

[51] Int. Cl.³ .................. C07D 211/16; C07D 207/24
[52] U.S. Cl. .............................. 546/246; 260/326.2; 424/267; 424/274
[58] Field of Search ...................... 546/246; 260/326.2

[56] References Cited

U.S. PATENT DOCUMENTS

| | | | |
|---|---|---|---|
| 3,794,652 | 2/1974 | Naito | 260/243.85 |
| 3,883,509 | 5/1975 | Fischer et al. | 260/239 B |

*Primary Examiner*—Leonard Schenkman

[57] ABSTRACT

Novel insecticidal sulfonium salts of 2-(alkylthio)ethyl esters of α-nitro-α-1-azacycloalk-2-ylidene) acetic acid.

3 Claims, No Drawings

INSECTICIDAL SULFONIUM SALTS

DESCRIPTION OF THE INVENTION

It has been found that useful insecticidal activity is possessed by certain sulfonium salts of the formula:

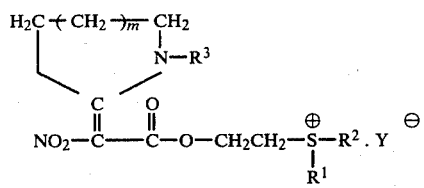 (I)

wherein m is 0 or 1, Y is an anion, $R^1$ is alkyl of 1 to 3 carbon atoms, $R^2$ is alkyl of 1 to 10 carbon atoms and $R^3$ is hydrogen or alkyl of from 1 to 3 carbon atoms.

These salts are resonance hybrids, and those in which $R^3$ is hydrogen may exist in the tautomeric enol forms, and all may exist as geometric isomers.

In this specification, for the sake of simplicity, these salts will be defined in terms of Formula (I). The definition is intended to include all of the contributors to the resonance hybrid, the geometric isomers and the enol forms, as well as mixtures thereof.

As described hereinafter, the salts of this invention can be prepared by treating the appropriate 2-($R^2$-thio)ethyl ester with the appropriate $R^1$-Y compound. The suitable $R^1$-Y compounds include those wherein Y is chlorine, bromine or iodine, alkyl sulfate (alkyl-$SO_4^-$), fluorosulfonate ($FSO_3^-$) or fluoborate ($BF_4^-$).

Because of their insecticidal activity characteristics, a preferred sub-genus of the genus of the invention consists of those compounds of the general formula wherein $R^1$ is methyl, $R^3$ is hydrogen and Y is chloride, bromide or iodide.

For illustration, preparation of a typical species esters of the genus is described in the example included hereinafter.

The salts of this invention are readily prepared by treating the corresponding 2-($R^2$-thio)ethyl esters with the appropriate compound $R^1$-Y, in a suitable solvent, at room temperature or moderately above—for example, up to 50° C.

The precursor 2-($R^2$-thio)ethyl esters can be prepared by the base-promoted transesterification of an alkyl ester

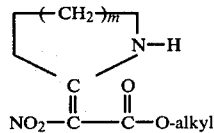

such as the methyl or ethyl ester, by treating the alkyl ester with at least two equivalents of an alkali metal alcoholate of the appropriate 2-($R^2$-thio)ethyl alcohol, in a solvent such as dimethylformamide. This may be done by treating the appropriate alcohol in the solvent with an alkali metal hydride, then adding the ester, also in the solvent. The reaction of the alcohol and hydride usually is exothermic so that cooling is usually needed to control the temperature of the reaction mixture. Reaction of the alcoholate with the ester ordinarily can be conducted at room temperature.

With either technique, recovery of the product is most effectively attained in most cases by quenching the final reaction mixture in water, treating the aqueous mixture with a suitable solvent such as ether to remove the solvent alcohol and other neutral organic species, then acidifying the aqueous phase. In some cases, the product ester crystallizes out of the water; in other cases, it can be recovered by extracting the water-phase with a suitable water-insoluble solvent such as methylene chloride or ethyl ether.

The precursor esters can be prepared by treating an alkoxy-2-$\Delta_1$-pyrroline or a 6-alkoxy-2,3,4,5-tetrahydropyridine with an alkyl ester of nitroacetic acid, at a moderately elevated temperature (e.g., about 50°–100° C.) to form the desired alkyl ester precursor.

Preparation of the precursor esters is illustrated in Example 1, hereinafter, for a species in which m is 1 and $R^3$ is hydrogen, from 6-methoxy-2,3,4,5-tetrahydropyridine. The corresponding esters wherein m is zero can be prepared from the corresponding alkoxy-2-$\Delta_1$-pyrrolines (U.S. Pat. No. 3,560,523; Belgian patent No. 1,383,784).

The precursor esters wherein $R^3$ is alkyl can be prepared in the same manner from lactam acetals, 1-$R^3$-2,2-di(alkoxy)piperidines (m=1) and -pyrrolidines (m=0), which can be prepared by a procedure set out in British Pat. No. 1,236,842, wherein the appropriate lactam (1-$R^3$-2-piperidone (m=1) or -pyrrolidone (m=0)) is treated with a dialkyl sulfate or trialkyloxonium fluoborate and the product treated with an alkoxide to yield the lactam acetal.

The procedure for preparing compounds of this invention are illustrated in the following example of the preparation of particular species of such compounds. In all cases the identity of the precursor(s) was established and the identity of the final product was confirmed, by elemental analysis and by infrared and nuclear magnetic resonance spectrum analyses:

EXAMPLE 1 dimethyl (2-(nitro(2-piperidinylidene)acetyloxy)ethyl)sulfonium iodide (1)

To a solution of 100 g of delta-valerolactam in 300 ml of refluxing benzene, 126 g of dimethyl sulfate was added over 2.5 hours and refluxing was continued for 16 hours. The two-phase system was cooled with an ice bath and slowly treated with excess 50% aqueous $K_2CO_3$ solution. The organic phase was separated; the aqueous phase was extracted twice with benzene, and the combined extracts was dried ($MgSO_4$). Evaporation of the solvent under reduced pressure followed by vacuum distillation gave 6-methoxy-2,3,4,5-tetrahydropyridine 1A as a colorless liquid, b.p. 568°–70° (50 Torr.).

A mixture of 13.1 g of methyl nitroacetate and 11.3 g of 1A was heated slowly to 80° and stirred at that temperature for 3 hours. The mixture then was cooled, ether was added and the mixture was filtered, the cream-colored solid being the methyl ester of nitro(2-piperidinylidene)acetic acid (1B), m.p.: 132°–133°. 40 g of 2-(methylthio)ethanol in 20 ml of dimethylformamide was added dropwise to 2.4 g of 57% mineral oil dispersion of sodium hydride in 40 ml of dimethylformamide at 0°. The mixture then was allowed to warm to room temperature and stirred for 30 minutes, then 5.0 g of 1B was added and the resulting mixture was stirred overnight at room temperature.

The mixture was poured into ice water and extracted with ether and methylene chloride. The extracts were combined and the solvent was evaporated under reduced pressure. The residue was partitioned between water and ether. The ether was evaporated from the extract under reduced pressure and the residue was treated with dilute acetic acid. The resulting yellow solid phase was the 2-(methylthio)ethyl ester of nitro(2-piperidinylidene)acetic acid (1C), m.p.: 96°–97°. 3 ml of methyl iodide was added to a solution of 0.5 g of 1C in 6 ml of acetone and the mixture was stirred at room temperature over a week-end. The solid phase was collected, washed with acetone and ether to give 1, as a pale yellow solid, m.p.: 118° (with decomposition).

The salts of this invention exhibit useful insecticidal activity, being of particular interest for control of the larval "caterpillar" or "worm" forms of lepidopterous insects of the genus Heliothis, such as *H. zea* (corn earworm), cottom bollworm, tomato fruitworm), *H. virescens* (tobacco budworm); the genus Agrotis, such as *A. ipsilon* (black cutworm); the genus Trichoplusia, such as *T. ni* (cabbage looper), and the genus Spodoptera, such as *S. littorails (Egyptian cotton leafworm)*.

The activity of the compound of Example 1 with respect to insects was determined by using standardized test methods to establish the $LC_{50}$ dosage (in milligrams of test compound per 100 milliliters of solvent or liquid carrier required in the solution or suspension of test compound used) that was required to kill 50% of the test insects. The test insects were the housefly, corn earworm, mosquito larvae, pea aphid and 2-spotted spider.

Compound 1 was found to be inactive with respect to the flies, aphids, mites and mosquito larvae, but quite active with respect to the corn earworms.

The invention includes within its scope insecticidal compositions comprising an adjuvant—that is, a carrier, optionally a surface-active agent—and, as active ingredient, at least one insecticide of this invention. Likewise the invention includes also a method of combatting insect pests at a locus which comprises applying to the locus an effective amount of at least one insecticide of the invention.

The term "carrier" as used herein means a material which may be inorganic or organic and of synthetic or natural origin with which the active compound is mixed or formulated to facilitate its application to the plant, seed, soil or other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates, for example, attapulgites and vermiculities; aluminum silicates, for example, kaolinites, monotmorillonites and micas; calcium carbonate; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychorophenols; bitumen, waxes such as beeswax, paraffin wax, and chlorinated mineral waxes; degradable organic solids, such as ground corn cobs and walnut shells; and solid fertilizers, for example, superphosphates.

Suitable liquid carriers include solvents for the salts of this invention and liquids in which the toxicant is insoluble or only slightly soluble.

Examples of such solvents and liquid carriers generally are water, alcohols, for example, isopropyl alcohol; ketones, such as acetone, methyl ethyl ketone, methyl isobutyl ketone and cyclohexanone; ethers; aromatic hydrocarbons such as benzene, toluene and xylene; petroleum fractions, such as kerosene, light mineral oils; chlorinated hydrocarbons, such as carbon tetrachloride, perchloroethylene, trichloroethane; including liquefied normally vaporous gaseous compounds. Mixtures of different liquids are often suitable.

If used, the surface-active agent may be an emulsifying agent or a dispersing agent or a wetting agent. It may be nonionic or ionic. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acid salts of low molecular weight, mono-, di- and trialkylamines; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products; alkali or alkaline earth metal salts, preferably sodium salts, of sulfuric or sulfonic acids esters containing at least 10 carbon atoms in the molecule, for example, sodium lauryl sulfate, sodium secondary alkyl sulfates, sodium salts of sulfonated caster oil, and sodium alkyaryl sulfonates such as sodium dodecylbenzene sulfate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerolsols. Encapsulated formulations and controlled release formulations also are contemplated, as are bait formulations. Wettable powders are usually compounded to contain 25, 50 or 75%w of toxicant and usually contain, in addition to solid carrier, 3–10%w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½–10%w of active ingredient. Granules may be manufactured by agglomeration or impregnation techniques. Generally, granules will contain ½–25%w active ingredient and 0–10%w of additives such as stabilizers, slow release modifiers and binding agents. Emulsifiable concentrates usually contain, in addition to the solvent, and when necessary, co-solvent, 10–50%w/v active ingredient, 2–20%w/v emulsifiers and 0–20%w/v of appropriate additives such as stabilizers, penetrants and corrosion inhibitors. Suspension concentrates are compounded so as to obtain a stable, non-sedimenting, flowable product and usually contain 10–75%w active ingredient, 0–5%w of dispersing agents, 0.1–10%w of suspending agents such as protective colloids and thixotropic agents, 0–10%w of appropriate additives such as defoamers, corrosion inhibitors, stabilizers, penetrants and stickers, and as carrier, water or an organic liquid in which the active ingredient is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention may also contain other ingredients, for example, other compounds possessing pesticidal, herbicidal or fungicidal properties, or attractants, such as pheromones, attractive food ingredients, and the like, for use in baits and trap formulations.

These compositions are applied in sufficient amount to supply the effective dosage of active ingredient at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect species to be controlled and the like, proper consideration and resolution of these factors to provide the necessary dosage of the active ingredient at the locus being within the skill of those versed in the art. In general, however, the effective dosage of salts of this invention at the locus to be protected—i.e. the dosage to which the insect contacts—is of the order of 0.001% to 0.5% based on the total weight of the formulation, though under some circumstances the effective concentration will be as little as 0.001% or as much as 2%, on the same basis.

What is claimed is:

1. A sulfonium salt of the formula:

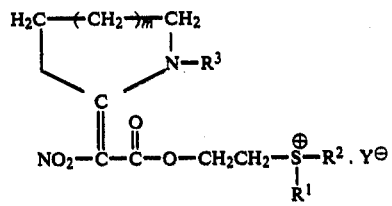

wherein m is 0 or 1, Y is an anion, $R^1$ is alkyl of 1 to 3 carbon atoms, $R^2$ is alkyl of 1 to 10 carbon atoms and $R^3$ is hydrogen or alkyl of from 1 to 3 carbon atoms.

2. A salt according to claim 1 wherein $R^1$ is methyl, $R^3$ is hydrogen and Y is chloride, bromide or iodide.

3. A salt according to claim 2 wherein $R^2$ is methyl.

* * * * *